(12) United States Patent
Muenster et al.

(10) Patent No.: US 9,128,200 B2
(45) Date of Patent: Sep. 8, 2015

(54) METHOD AND APPARATUS FOR DETECTING A PARTICULAR MATERIAL IN AN OBJECT BY MEANS OF ELECTROMAGNETIC RADIATION

(75) Inventors: Matthias Muenster, Wiesbaden (DE); Joerg Nittikowski, Hohenstein (DE); Pia Dreiseitel, Eschborn (DE); Andreas Mader, Trebur (DE); Rainer Heinkel, Schweppenhausen (DE); Thomas Ries, Gruendau (DE); Dirk Naumann, Lorsch (DE); Uwe Siedenburg, Essenheim (DE)

(73) Assignee: Smiths Heimann GmbH, Wiesbaden (DE)

(*) Notice: Subject to any disclaimer, the term of this patent is extended or adjusted under 35 U.S.C. 154(b) by 695 days.

(21) Appl. No.: 12/906,437

(22) Filed: Oct. 18, 2010

(65) Prior Publication Data

US 2011/0091013 A1    Apr. 21, 2011

Related U.S. Application Data

(63) Continuation of application No. PCT/EP2009/002603, filed on Apr. 8, 2009.

(30) Foreign Application Priority Data

Apr. 18, 2008 (DE) .......................... 10 2008 019 754

(51) Int. Cl.
*G01V 5/00* (2006.01)
*G01N 23/04* (2006.01)
*G01N 23/087* (2006.01)
*G01N 23/10* (2006.01)

(52) U.S. Cl.
CPC .............. *G01V 5/0058* (2013.01); *G01N 23/04* (2013.01); *G01N 23/087* (2013.01); *G01N 23/10* (2013.01); *G01V 5/0016* (2013.01); *G01N 2223/401* (2013.01); *G01N 2223/633* (2013.01); *G01N 2223/639* (2013.01)

(58) Field of Classification Search
CPC ... G01N 23/04; G01N 23/046; G01N 23/083; G01N 23/087; G01N 23/10; G01N 2223/04; G01N 2223/304; G01N 2223/401; G01N 2223/402; G01N 2223/405; G01N 2223/41; G01N 2223/601; G01N 2223/606; G01N 2223/633; G01N 2223/639; G01N 2223/643; G01V 5/0008; G01V 5/0016
See application file for complete search history.

(56) References Cited

U.S. PATENT DOCUMENTS 5,367,552 A * 11/1994 Peschmann ...................... 378/57
5,838,758 A * 11/1998 Krug et al. ...................... 378/53

(Continued)

FOREIGN PATENT DOCUMENTS

WO    WO 03/031960 A2    4/2003

*Primary Examiner* — Thomas R Artman
(74) *Attorney, Agent, or Firm* — Muncy, Geissler, Olds & Lowe, P.C.

(57) ABSTRACT

A method and apparatus is provided for detection of a particular material in an object, in particular in an item of luggage, by means of electromagnetic radiation in which the intensities of non-absorbed radiation from at least three radiation planes are measured and evaluated in associated detector apparatus, wherein an image is produced, initially from the intensities of the non-absorbed radiation, and then if single regions of low complexity are found which are characterized by approximately constant intensities, an estimation of the attenuation coefficient s performed and a material detection is carried out in the region according to an algorithm which calculates a three-dimensional reconstruction from different views.

11 Claims, 2 Drawing Sheets

(56) References Cited

U.S. PATENT DOCUMENTS

| | | | |
|---|---|---|---|
| 6,018,562 A * | 1/2000 | Willson | 378/9 |
| 6,088,423 A * | 7/2000 | Krug et al. | 378/57 |
| 6,567,496 B1 * | 5/2003 | Sychev | 378/57 |
| 7,020,241 B2 | 3/2006 | Beneke et al. | |
| 7,221,732 B1 * | 5/2007 | Annis | 378/57 |
| 2008/0025464 A1 * | 1/2008 | Foland et al. | 378/57 |
| 2008/0063140 A1 * | 3/2008 | Awad | 378/57 |
| 2008/0304622 A1 * | 12/2008 | Morton | 378/51 |

\* cited by examiner

METHOD AND APPARATUS FOR DETECTING A PARTICULAR MATERIAL IN AN OBJECT BY MEANS OF ELECTROMAGNETIC RADIATION

This nonprovisional application is a continuation of International Application No. PCT/EP2009/002603, which was filed on Apr. 8, 2009, and which claims priority to German Patent Application No. DE 10 2008 019 754.8, which was filed in Germany on Apr. 18, 2008, and which are both herein incorporated by reference.

BACKGROUND OF THE INVENTION

1. Field of the Invention

The invention relates to a method and an apparatus for detecting a particular material in an object, particularly in a piece of luggage, by means of electromagnetic radiation, in which the intensities of unabsorbed radiation from at least three radiation planes are measured and evaluated in associated detector devices.

2. Description of the Background Art

Methods and apparatus for the inspection of objects are used, in which the object is conveyed through electromagnetic radiation, emitted by stationary radiation sources, as is well-known, for example, for security inspection of pieces of luggage at airports. The intensities of the unabsorbed radiation are measured and evaluated by the likewise stationary detector devices assigned to the radiation sources. Typically, the inspection occurs with use of x-rays.

A method is disclosed in WO 03/031960, which corresponds to U.S. Pat. No. 7,020,241, and which is incorporated herein by reference, and in which five stationary radiation sources emit x-rays in radiation planes, three of which run parallel to one another and perpendicular to the transport direction of the objects through the luggage inspection device. It is verified according to the following method from the data of the detector devices associated with the radiation sources whether a suspected material is also actually present:

First, a two-dimensional image of the object is produced and then an area shown on the image based on the value of a material variable is selected for checking; an absorption thickness of the area is then determined with use of a stored value, and concurrently the corresponding thickness of the area is determined from spatial position data, which were determined solely from the measured intensity values. It is then determined by a comparison of the two determined values whether the suspected material is in fact present. In the method, the intensities of two energy ranges are evaluated separately in a known manner in the so-called dual-energy method, x-rays being evaluated in energy ranges below (low range) and above (high range) about 70 keV.

This advantageous method works differently from known computer tomographs with a low number of less than 10 views, which are produced with a suitable number of stationary radiation sources and stationary detectors. A complex object cannot be fully reconstructed for mathematical reasons with this low number of views. Therefore, this method is restricted to the obtainment of partial information from particular regions, which are selected from single views and checked further.

SUMMARY OF THE INVENTION

It is therefore an object of the invention is to create a method of the generic type, which enables a precise evaluation and thereby an improved detection performance. A further object is to provide an apparatus for carrying out a method of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
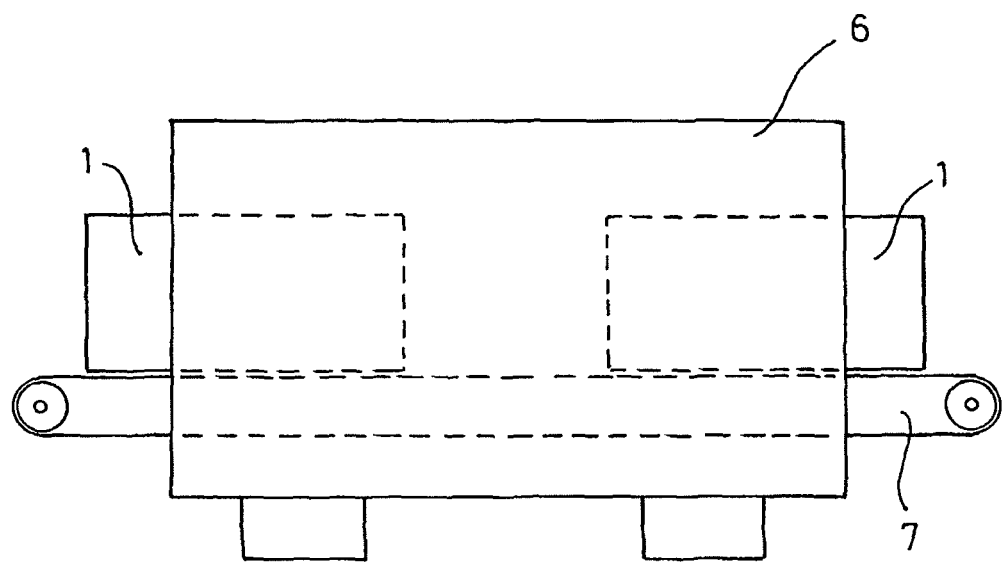
FIG. 1 shows the basic structure of the apparatus.

The device depicted in FIG. 1 serves as a testing unit for security inspection of objects 1, particularly of pieces of luggage, as it is carried out at airports. In so doing, items 2 located in the pieces of luggage are checked in regard to their security relevance.

The test unit contains as basic components stationary radiation sources 3.1-3.4 and the same number of associated detector devices, by which the intensities of the radiation not absorbed by object 1 are measured. At least three radiation sources 3.1-3.4 and associated detector devices are used; preferably, there are 4 to 15 radiation sources, particularly 4 to 8; there are 4 in the example. Radiation sources 3.1.-3.4 are arranged here such that objects 1 are x-rayed in each case in different directions, to obtain as much independent data as possible. For this purpose, radiation sources 3.1-3.4 are arranged in the transport direction of objects 1 at a distance behind one another and on different sides of the radiation tunnel 6, through which objects 1 are transported by a transport apparatus, preferably a belt conveyor 7. In this regard, rays are emitted in at least three, preferably fan-shaped radiation planes 5.1-5.4, which are preferably parallel to one another. Preferably, x-rays are emitted within an energy range up to a maximum of 140 keV. The detector devices contain double detectors, which for the so-called dual-energy method measure the intensities of the unabsorbed radiation separately by high (>70 keV) and lower (<70 keV) energies.

Further, the test unit contains an evaluation unit with a computer and a screen, on which the generated images of objects 1 and the items 2 located therein are shown for an additional visual examination by an operator. Evaluation software is stored in the computer, which checks whether items 2 made of a particular material are present in objects 1 according to the method described below:

First, object 1 to be examined is conveyed by conveyor 7 into the examination area (radiation tunnel 6), where it is x-rayed by x-rays from the x-ray sources in at least three radiation planes. The radiation not absorbed by object 1 is taken up by the associated x-ray detectors, converted into electrical signals, which are digitized, and an image is produced by the dual-energy method, which contains particular material information. A dual-energy method is not absolutely necessary, if the measurement in only one energy range is sufficient for determining the desired material information.

The x-ray image of the examined object 1 produced in a first evaluation step is now classified in a second evaluation step with respect to its complexity. Parameters for this classification can be: a metal part determined in step 1 in the examination area, its brightness, and the proportion and size of areas with the same intensity.

Figure 2:
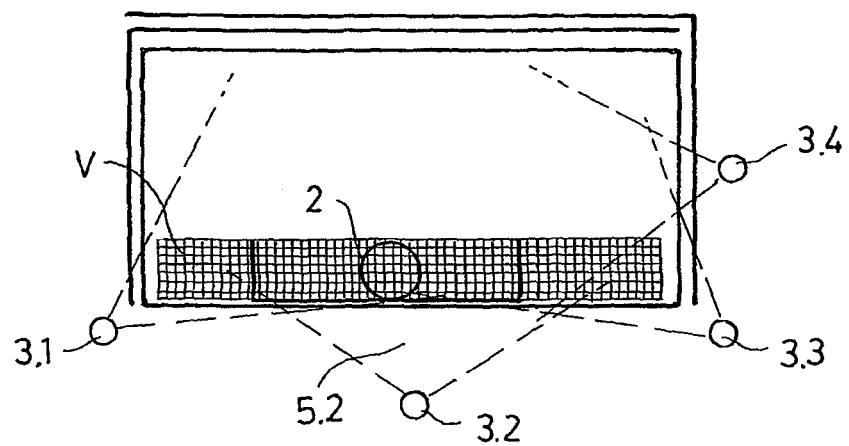
FIG. 2 shows a sectional view through an apparatus in which the object is x-rayed by four radiation sources.
Figure 3:
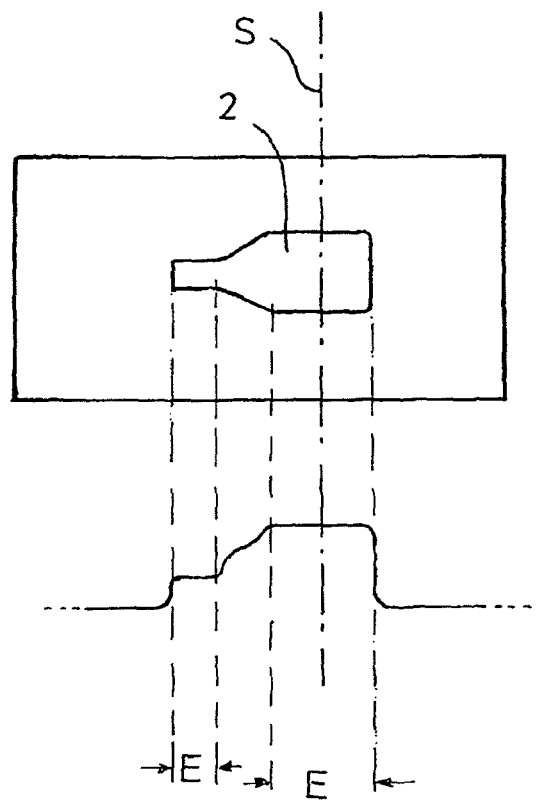
FIG. 3 shows the x-ray image of the object from which the complexity is determined.
Figure 4:
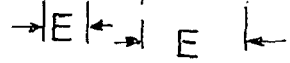
FIG. 4 shows the associated mass profile.

An advantageous method for determining the complexity is sketched in FIGS. 3 and 4. In this method, simple areas E of low complexity within object 1 are determined so that a mass profile is generated. To this end, for the different layers of object 1, which are taken through the radiation planes, in each case the unabsorbed intensities measured by each detector unit are added together. Preferably, the radiation planes and therefore also the layers, to be examined, of an object 1 run perpendicular to belt conveyor 7, as shown in FIGS. 2 and 3. The addition of the unabsorbed intensities produces the profile for an object 1 as shown in FIG. 4. It is checked here whether or not low complex, simple areas E are present in which the summed values of the intensities change only slightly or not at all.

If simple areas E are found, then the further evaluation occurs according to an algorithm, which calculates a three-dimensional reconstruction of object 1 to be examined from the different views and performs a material detection by estimation of the attenuation coefficient $\mu$.

To this end, first a layer S to be examined is selected, which extends through the area E of simple complexity. The area to be examined in layer S is divided into a voxel grid V. The individual voxels in this regard can be block-shaped with an edge length of about 3.5 mm and a depth that corresponds to the width of a detector row. The number of voxels to be examined is determined before the evaluation. Depending on the position of radiation sources 3.1-3.4 and the selected area, the passage length of the x-rays through the selected voxels is then determined. With use of the passage length as an absorption thickness, finally the attenuation coefficient $\mu$ is determined by using the high-energy radiation with the aid of the absorption equation. The attenuation coefficient $\mu$ is characteristic for the materials to be detected during the inspection.

In the images of objects, classified as complex, an algorithm is used to determine the material from the ratio of the absorption values at different x-ray energies.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for detecting a particular material in an object via electromagnetic radiation, in which intensities of unabsorbed radiation from at least three radiation planes are measured and evaluated in associated detector devices, the method comprising:
   measuring intensities of the unabsorbed radiation of the object by each of the at least three radiation planes;
   producing a two-dimensional image from the measured intensities of the unabsorbed radiation;
   identifying areas of the two-dimensional image of the object using the produced two-dimensional image based on the measured intensities of the unabsorbed radiation of the object;
   from the identified areas, determining an area of the object with an approximately constant intensity of the unabsorbed radiation of the object and an area of the object with varying intensity of the unabsorbed radiation;
   reconstructing a three-dimensional image of the object using the two-dimensional image of the object produced by each of the at least three radiation planes; and
   selecting the area of the object with the approximately constant intensity of the unabsorbed radiation and detecting a material of the object in said selected area of the object with the approximately constant intensity of the unabsorbed radiation by an estimation of an attenuation coefficient,
   wherein the approximately constant intensity is of an intensity with only a slight change or no change at all.

2. The method according to claim 1, wherein the object is luggage.

3. The method according to claim 1 wherein if the area of varying intensity of said unabsorbed radiation are determined, measuring said unabsorbed radiation using two different radiation levels of intensity.

4. The method according to claim 3 wherein the ratio of absorption values of said two different radiation level is measured to determine material in said area of varying intensity of said unabsorbed radiation.

5. The method according to claim 1, wherein the areas of the two-dimensional image of the object are identified based on a parameter that includes a metal part detected based on the measured intensity, a brightness, a proportion and size of areas with the same intensity.

6. The method according to claim 1, wherein each of the area of the object with the approximately constant intensity of the unabsorbed radiation of the object and the area of the object with varying intensity of the unabsorbed radiation is defined by a constant/varying intensity starting point and a constant/varying intensity ending point in the two-dimensional image of the object.

7. An apparatus comprising:
   a transport device conveying through a radiation tunnel;
   radiation sources arranged around the transport device that are configured to emit rays in at least three radiation planes;
   a detector unit that is associated with each of the radiation sources; and
   an evaluation unit that includes a computer that has software, when the software is executed on the computer, the evaluation unit is caused to:
   measure intensities of the unabsorbed radiation of the object detected by the detector unit,
   produce a two-dimensional image from the measured intensities of unabsorbed radiation,
   identify areas of the two-dimensional image of the object using the produced image based on the measured intensities of said unabsorbed radiation of the object,
   from the identified areas, determine an area of the object with an approximately constant intensity of the unabsorbed radiation of the object and an area of the object with varying intensity of the unabsorbed radiation,
   reconstruct a three-dimensional image of the object using the two-dimensional image of the object produced by each of the at least three radiation planes, and
   select the area of the object with the approximately constant intensity of the unabsorbed radiation and detect a material of the object in said selected area of the object with the approximately constant intensity of the unabsorbed radiation by an estimation of an attenuation coefficient, wherein the approximately constant intensity is of an intensity with only a slight change or no change at all.

8. The apparatus according to claim 7 wherein if the area of varying intensity of said unabsorbed radiation are determined, measuring said unabsorbed radiation using two different radiation levels of intensity.

9. The apparatus according to claim 8 wherein the ratio of absorption values of said two different radiation level is measured to determine material in said area of varying intensity of said unabsorbed radiation.

10. The apparatus according to claim 7, wherein the evaluation unit identifies the areas of the two-dimensional image of the object based on a parameter that includes a metal part detected based on the measured intensity, a brightness, a proportion and size of areas with the same intensity.

11. The apparatus according to claim 7, wherein each of the area of the object with the approximately constant intensity of the unabsorbed radiation of the object and the area of the object with varying intensity of the unabsorbed radiation is defined by a constant/varying intensity starting point and a constant/varying intensity ending point in the two-dimensional image of the object.

\* \* \* \* \*